United States Patent [19]

Sato et al.

[11] Patent Number: 4,659,710

[45] Date of Patent: Apr. 21, 1987

[54] 1,7-NAPHTHYRIDINE DERIVATIVES AND PHARMACEUTICAL COMPOSITIONS

[75] Inventors: Susumu Sato; Haruyoshi Honda; Teruo Koumoto, all of Chiba; Kazuo Isomae, Narashino; Tadayuki Kuraishi, Chiba; Tatsuhiko Katori, Tonemachi, all of Japan

[73] Assignee: SS Pharmaceutical Co., Ltd., Tokyo, Japan

[21] Appl. No.: 850,820

[22] Filed: Apr. 11, 1986

[30] Foreign Application Priority Data

Apr. 17, 1985 [JP] Japan .................................. 60-81967

[51] Int. Cl.$^4$ .................. A61K 31/44; A61K 31/535; C07D 221/00; C07D 413/14
[52] U.S. Cl. .................................... 514/234; 514/254; 514/300; 544/117; 544/362; 546/122
[58] Field of Search ................ 544/117, 362; 546/122; 514/234, 254, 300

[56] References Cited

U.S. PATENT DOCUMENTS 3,928,367 12/1975 Mayer et al. ...................... 546/122
4,176,183 11/1979 Baldwin et al. .................... 514/233

*Primary Examiner*—Robert W. Ramsuer
*Attorney, Agent, or Firm*—Oblon, Fisher, Spivak, McClelland & Maier

[57] ABSTRACT

Certain 1,7-naphthyridine derivatives and their acid addition salts have strong antiarrhythmic effects, cardiotonic effects, diuretic effects, bronchodilation effects, anti-acetylcholine effects, anti-inflammatory effects, analgesic effects and the like and are hence useful for various diseases such as heart diseases, hypertension, asthma, arthritis, lumbago, toothache, etc.

2 Claims, No Drawings

1,7-NAPHTHYRIDINE DERIVATIVES AND PHARMACEUTICAL COMPOSITIONS

BACKGROUND OF THE INVENTION

1. Field of the Invention

This invention relates to novel 1,7-naphthyridine derivatives, and more specifically to novel 1,7-naphthyridine derivatives and their acid addition salts, which are all useful as pharmaceutical products.

2. Description of the Prior Art

Many 1,7-naphthyridine derivatives have been known to date. Of these, derivatives having certain pharmacological effects are limited to those having hypotensive effects (U.S. Pat. No. 4,176,183) and those having insecticidal effects (German Offenlegungsschrift No. 2,361,438). No other 1,7-naphthyridine derivatives having one or more pharmacological effects have been reported.

SUMMARY OF THE INVENTION

An object of this invention is to provide 1,7-naphthyridine derivatives having certain pharmacological effects.

Another object of this invention is to provide medicinal preparations containing such pharmacologically-effective 1,7-naphthyridine derivatives as effective components.

The present inventors synthesized a variety of 1,7-naphthyridine derivatives and studied their pharmacological effects. As a result, it has been found that the novel compounds represented by the general formula (I) have strong antiarrhythmic effects, cardiotonic effects, diuretic effects, bronchodilation effects, anti-acetylcholine effects, anti-inflammatory effects, analgesic effects and the like and are hence useful for various diseases such as heart diseases, hypertension, asthma, arthritis, lumbago, toothache, etc., leading to completion of this invention.

In one aspect of this invention, there is thus provided a 1,7-naphthyridine derivative represented by the following general formula (I):

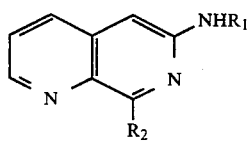

(I)

wherein $R_1$ means a hydrogen atom or a $COR_3$ group; in which $R_3$ is an alkyl group, a phenyl group which may optionally be substituted by one or more alkyl, alkoxy, hydroxyl and/or halogen, or a styryl group, and $R_2$ denotes an alkoxy, piperidino or morpholino group, an

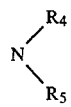

group, in which $R_4$ is a hydrogen atom or an alkyl or hydroxyethyl group and $R_5$ is an alkyl, amino, hydroxyethyl, hydroxypropyl, dihydroxypropyl, dialkylaminoethyl, phenylethyl, alkoxyphenylethyl or pyridylmethyl group, or an

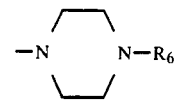

group, in which $R_6$ is an alkyl, phenyl or hydroxyethyl group or a cinnamoyl group which may optionally be substituted by one or more alkyl, alkoxy and/or hydroxyl groups and/or halogen atoms, with a proviso that $R_2$ is other than a methoxy or ethoxy group when $R_1$ stands for a hydrogen atom; or an acid addition salt thereof.

In another aspect of this invention, there is also provided a medicinal preparation, especially, an anti-inflammatory agent or a medicinal preparation for circulatory organs, which contains the 1,7-naphthyridine derivative (I) or its acid addition salt.

The 1,7-naphthyridine derivatives (I) and their acid addition salts have strong antiarrhythmic effects, cardiotonic effects, diuretic effects, bronchodilation effects, anti-acetylcholine effects, anti-inflammatory effects, analgesic effects and the like and are hence useful for various diseases such as heart diseases, hypertension, asthma, arthritis, lumbago, toothache, etc.

The above and other objects, features and advantages of this invention will become apparent from the following description and the appended claims.

DETAILED DESCRIPTION OF THE INVENTION AND PREFERRED EMBODIMENTS

The compound of this invention which is represented by the general formula (I) can, for example, be prepared by the following process.

(Process)

The compound (I) is obtained by reacting a 1,7-naphthyridine derivative (II) with a compound represented by the general formula (III).

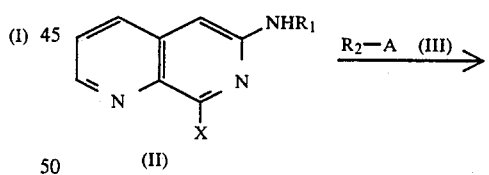

(II)

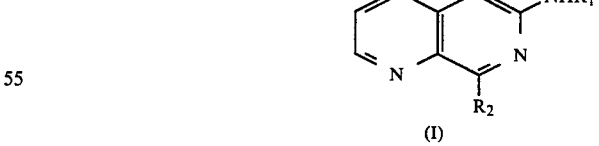

(I)

wherein X means a halogen atom, A denotes a hydrogen atom or alkali metal, and $R_1$ and $R_2$ have the same meaning as defined above.

The above reaction is carried out either by stirring the reactants for several hours to several days at room temperature or the reflux temperature of a solvent to be used or by heating them for several hours to several days in a sealed tube. The reaction may be conducted in the presence of a base such as sodium hydride, sodium hydroxide or potassium hydroxide if necessary. As the solvent, may be mentioned methanol, ethanol, an water-containing alcohol, acetone, dimethyl formamide, dioxane, ethoxy ethanol or the like.

Among the 1,7-naphthyridine derivatives (II) useful as starting materials in the above reaction, those represented by the general formula (II) in which $R_1$ stands for a hydrogen atom can be easily obtained by processes known per se in the art [Rosita Tan: Tetrahydron Letters, 1233–1237 (1966)].

Of the 1,7-naphthyridine derivatives (II), derivatives (II'') represented by the general formula (II) in which $R_1$ stands for an acyl, benzoyl or cinnamoyl group are novel compounds. They can each be prepared, for example, by reacting the 6-amino-8-bromo(or chloro)-1,7-naphthyridine derivative (II') with its corresponding carboxylic acid or a reactive derivative thereof in the presence of a base in accordance with the following reaction formula.

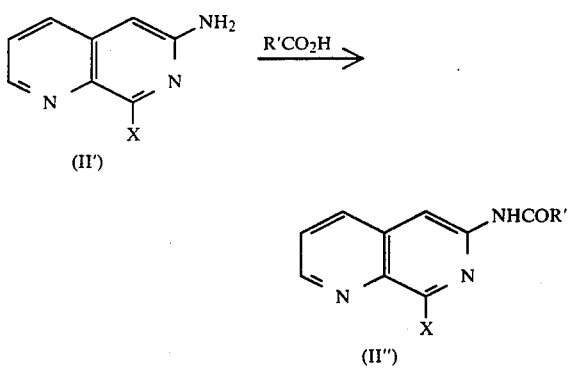

wherein X means a halogen atom, and R' denotes an alkyl group; a phenyl group which may optionally be substituted by one or more alkyl, alkoxy, hydroxyl and/or halogen, or a styryl group.

The above reaction is effected by a usual acylation process.

The thus-obtained 1,7-naphthyridine derivatives (I) of this invention may be converted, by methods known per se in the art, to their inorganic acid salts such as hydrochlorides hydrobromides and sulfates or organic acid salts such as maleates, fumarates, tartrates, citrates and methanesulfonates as needed.

Pharmacological effects and toxicity of the compounds of this invention, which had been obtained in the above manner, were tested. Test results will next be described.

(1) Anti-inflammatory effects:

After fasting a group of five Wistar rats of 6 weeks old for 18 hours, each test compound dissolved or suspended in a 0.5% solution of sodium carboxymethylcellulose (CMC-Na) was administered orally. Sixty minutes after the administration of the test compound, 0.1 ml of a 1% carrageenan solution was injected into subplanter surface of the right hind paw of each rat. The foot volume (A) was measured 3 hours later. From the foot volume (B) before the administration of carrageenan, the percent swelling ((A−B)/B×100) was calculated and compared with those of control rats.

The swelling inhibitory effect of each test compound was demonstrated by swelling inhibition (%) which was calculated by the following equation. Inhibition (%)=

$$\left(1 - \frac{\text{Percent swelling of test compound group}}{\text{Percent swelling of control group}}\right) \times 100$$

Results are shown in Table 1.

TABLE 1

| Compound No. | Dose (mg/kg) | Inhibition (%) |
|---|---|---|
| 3 | 100 | 55.0 |
| 4 | 30 | 54.0 |
| 9 | 30 | 27.1 |
| 22 | 10 | 42.4 |
| 25 | 10 | 44.6 |

As apparent from the above results, the compounds (I) of this invention have strong anti-inflammatory effects and are hence useful as anti-inflammatory agents.

(2) Antiarrhythmic effects:

Using a group of five Hartley male guinea pigs (body weights: 530–990 g), their electrocardiograms were recorded from a limbic lead II under anesthesia with urethane 1.2 g/kg i.p. to investigate the antiarrhythmic effects. Namely, each test compound dissolved in 0.1N hydrochloric acid and diluted with a physiological saline was intravenously administered at a dose of 10 mg/kg. Immediately after the administration of the test compound, ouabain was continuously infused at a rate of 4 μg/kg/min through a polyethylene cannula inserted in the jugular vein of the guinea pigs so as to induce arrhythmia. The antiarrhythmic effects were judged from the amount of ouabain required to induce unequal intervals of R-R wave, ventricular extrasystole or A-V block, ventricular fibrillation and cardiac arrest. Result are shown in Table 2.

TABLE 2

| Test compound | Unequal intervals | Extrasystol or A-V block | Ventricular fibrillation | Cardiac arrest |
|---|---|---|---|---|
| Compound No. 4 | 59.1 | 78.9 | 216.5 | 277.5 |
| Compound No. 19 | 68.9 | 146.0 | — | 392.1 |
| Compound No. 22 | 69.6 | 109.6 | 285.4 | 399.3 |
| Control | 59.2 | 80.5 | 170.0 | 246.6 |

(3) Cardiotonic effects:

The heart of a Hartley male guinea pig having a body weight of 500–800 g was removed. Its atrial muscles were isolated in Krebs-Henseleit's solution. A spontaneously-beating atrial muscle was suspended, in a bath containing 20 ml of Krebs-Henseleit's solution gassed with 95% $O_2$+5% $CO_2$ at 32° C. Thereafter, the contractile force and its heart rate were measured. After stabilization, test compounds which were dissolved in a small amount of 1N hydrochloric acid or 0.1N hydrochloric acid and then diluted with a physiological saline, were administered cumulatively ($10^{-6}$–$10^4$ g/ml) to evaluate effects on the contractile force. The maximum percent change in increase of the contractile force induced by test compounds was determined and regarded as an index for cardiotonic (positive inotropic) effects. Heart rate increasing or decreasing effects (positive or negative chronotropism) were also observed. Results are shown in Table 3.

TABLE 3

| Test Compound | Inotropy and chronotropy, % of Control Spontaneously beating atria in G-Ps | | | | |
|---|---|---|---|---|---|
| | $10^{-6}$ | $3 \times 10^{-6}$ | $10^{-5}$ | $3 \times 10^{-5}$ | $10^{-4}$ |
| Comp'd No. 5 | 4.7 | 8.6 | 12.9 | 29.0 | 59.1 |
| | (1.7) | (3.6) | (5.9) | (8.6) | (13.0) |
| Comp'd No. 8 | 4.1 | 9.6 | 16.4 | 33.4 | 64.1 |
| | (1.1) | (2.7) | (4.0) | (6.8) | (12.9) |
| Comp'd No. 13 | 2.6 | 8.7 | 24.6 | 52.3 | 92.9 |
| | (0.2) | (1.6) | (3.1) | (1.9) | (−11.8) |
| Comp'd No. 16 | — | 4.5 | 12.5 | 36.8 | 103.2 |
| | | (1.6) | (3.3) | (7.0) | (19.0) |
| Comp'd No. 34 | 6.3 | 13.3 | 24.9 | 38.7 | 89.2 |
| | (5.3) | (10.3) | (18.5) | (25.7) | (46.0) |

(4) Acute toxicity:

Acute toxicity levels measured on certain representative compounds of this invention are shown in Table 4.

TABLE 4

| | $LD_{50}$ (mg/kg · p.o.) | |
|---|---|---|
| | Mouse | Rat |
| Compound No. 4 | >1000 | — |
| Compound No. 13 | >500 | — |
| Compound No. 16 | >500 | — |
| Compound No. 22 | 1600 | >3000 |

As has been described above, the 1,7-naphthyridine derivatives (I) of this invention have excellent anti-inflammatory effects, antiarrhythmic effects, cardiotonic effects and the like and moreover, are safe as demonstrated by their acute toxicity levels ($LD_{50}$) as high as at least 500 mg/kg. They are hence useful as anti-inflammatory agents and medicinal preparations for circulatory organs.

As preparation forms suitable for use upon administration of the compounds (I) of this invention, they may be formed into various preparation forms in accordance with the manner of their administration such as oral administration, parenteral administration, etc., for example, orally dosable preparations such as tablets, capsules, powders, granules and solutions and parenteral administrations such as cutaneous, intramuscular and intravenous injections, mixed transfusional solutions and suppositories.

The formulation of the compounds (I) of this invention into the above-mentioned dosable preparations can be carried out by methods known per se in the art. Namely, the 1,7-naphthyridine derivatives (I) or their salts can be obtained in the form of tablets, capsules, powders or granules by formulating them suitably along with an excipient such as starch, lactose or mannitol, a binder such as sodium carboxymethylcellulose or hydroxypropylcellulose, a disintegrator such as crystalline cellulose or calcium carboxymethylcellulose, a lubricant such as talc or magnesium stearate, a fluidity improver such as light silicic anhydride and/or the like. Their injections or solutions can be obtained in the form of oil-base injections by either suspending or dissolving the 1,7-naphthyridine derivatives (I) or their salts in a vegetable oil or the like or in the form of syrups by either dissolving or suspending them in water or the like by a method known per se in the art. They can also be obtained in the form of suppositories by dispersing them in a base employed routinely, for example, cacao butter, a synthetic fat or the like by a method known per se in the art and then solidifying the resultant mixtures.

Although the dose of each of the 1,7-naphthyridine derivatives (I) of this invention may be chosen suitably depending on the kind of each disease, the manner of medication, the age, sex and other conditions of each patient, the seriousness of the disease and so on, it is generally preferred to administer it in one to several portions at a daily dose of 0.1–20 mg/kg.adult in the case of oral administration or at a daily dose of 0.05–10 mg/kg.adult in the case of parenteral administration.

EXAMPLES

The present invention will hereinafter be described further by the following Referential Examples and Comparative Examples.

REFERENTIAL EXAMPLE 1

6-Acetamido-8-bromo-1,7-naphthyridine

Suspended in 32 ml of pyridine was 4.84 g of 6-amino-8-bromo-1,7-naphthyridine, followed by an addition of 66 ml of acetic anhydride. The resultant mixture was stirred at room temperature for 4 hours. After the reaction, the reaction mixture was poured in 500 ml of ice water and crystals, which precipitated out, were collected by filtration and then washed thoroughly with water. They were recrystallized from methanol to obtain 5.37 g of 6-acetamido-8-bromo-1,7-naphthyridine as colorless needle-like crystals (yield: 93.4%).

NMR δppm (DMSO-$d_6$): 11.0 (b.1H), 8.9 (d.d.1H), 8.5 (s.1H), 8.4 (d.d.1H), 7.7 (d.d.1H), 2.2 (s.3).

EXAMPLE 1

6-Amino-8-morpholino-1,7-naphthyridine

To a mixture of 800 mg of 6-amino-8-bromo-1,7-naphthyridine and 3.12 g of morpholine, 40 ml of methanol was added. The resultant mixture was refluxed for 13 hours. After the reaction, methanol was distilled off under reduced pressure and chloroform was added to the residue. After washing the chloroform solution with water, it was dried with anhydrous magnesium sulfate. Chloroform was distilled off under reduced pressure and a small amount of acetone was added to the residue to dissolve same. Hexane was then added to the residue, followed by removal of insoluble matter by filtration. The filtrate was concentrated and the residue was recrystallized from a mixed solvent of chloroform and hexane, thereby obtaining 500 mg of 6-amino-8-morpholino-1,7-naphthyridine (Compound No. 3) as yellowish crystals (yield: 60.9%).

EXAMPLE 2

6-Acetamido-8-[4-(2-hydroxyethyl)-1-piperazinyl]-1,7-naphthyridine

To a mixture of 2.66 g of 6-acetamido-8-bromo-1,7-naphthyridine and 6.51 g of 1-piperazine ethanol, 180 ml of ethoxyethanol was added. The resultant mixture was refluxed with stirring for 45 minutes. After the reaction, ethoxyethanol was distilled off under reduced pressure and chloroform was added to the residue. After thoroughly washing the chloroform solution with water, it was dried with anhydrous magnesium sulfate. Chloroform was distilled off under reduced pressure and the residue was purified by silica gel column chromatography, followed by recrystallization from a mixed solvent of ethanol and ether to obtain 2.6 g of 6-acetamido-8-[4-(2-hydroxyethyl)-1-piperazinyl]-1,7-naphthyridine (Compound No. 22) as light yellowish crystals (yield: 82.5%).

EXAMPLE 3

6-(4-Chlorobenzoylamino)-8-[4-(2-hydroxyethyl)-1-piperazinyl]-1,7-naphthyridine hydrochloride Dissolved in 20 ml of ethanol was 4.1 g of 6-(4-chlorobenzoylamino)-8-[4-(2-hydroxyethyl)-1-piperazinyl]-1,7-naphthyridine, followed by a gradual addition of HCl-saturated ethanol while stirring the reaction system under ice-cooling. Thereafter, 200 ml of ether was added further and the resultant crystals were collected by filtration. The crystals were thoroughly washed with ether and then dried, thereby obtaining 4.2 g of the hydrochloride (Compound No. 29) as light yellowish crystals.

Melting point: 248°–251° C. (decomposed).

EXAMPLE 4

Following the procedure of Example 1, 2 or 3, there were obtained compounds shown in Table 5, in which the compounds obtained in Examples 1, 2 and 3 are also shown.

TABLE 5

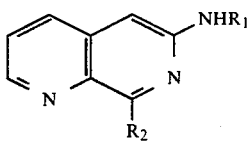

| Compound No. | $R_1$ | $R_2$ | NMR (δ ppm) | Melting point (°C.) HCl salt |
|---|---|---|---|---|
| 1 | H | —N(CH₃)₂ | 8.4(d.d.1H), 7.6(d.d.1H), 7.2(d.d.1H), 6.0(s,1H), 3.4(s,6H), 3.2–3.8(b.2H). | 207.0–210.0 (decomp.) |
| 2 | H | —N(piperidinyl) | 8.4(d.d.1H), 7.6(d.d.1H), 7.1(d.d.1H), 6.0(s.1H), 4.0–4.7(b.2H), 3.9(m.2H), 1.7(b.6H). | 123.5–124.5 |
| 3 | H | —N(morpholinyl) | 8.5(d.d.1H), 7.8(d.d.1H), 7.4(d.d.1H), 6.2(s.1H), 4.0–4.7(b.2H), 4.0(b.8H). | 112.5–113.5 |
| 4 | H | —N(piperazinyl)N—CH₂CH₂OH | 8.3(d.d.1H), 7.6(d.d.1H), 7.1(d.d.1H), 6.0(s.1H), 3.8–4.2(m.4H), 3.6(b.4H), 2.4–2.9(m.6H). | 160.0–163.0 (decomp.) |
| 5 | COCH₃ | —NHCH₃ | 8.4(d.d.1H), 7.8(d.d.1H), 7.5(s.1H), 7.3(d.d.1H), 6.7–7.0(m.1H), 3.05(d.3H), 2.15(s,3H). | 157.0–159.0 |
| 6 | COCH₃ | —NHC₃H₇ | 8.55(d.d.1H), 7.9(d.d.1H), 7.6(s.1H), 7.35(d.d.1H), 6.6–7.0(m.1H), 3.5(q.2H), 2.15(s.3H), 1.4–2.0(m.2H), 1.0(t.3H). | 130.5–132.0 |
| 7 | COCH₃ | —NHCH₂CH₂OH | 9.0(b.1H), 8.55(d.d.1H), 7.95(d.d.1H), 7.6(s.1H), 7.1–7.6(m.1H), 7.4(d.d.1H), 4.3–4.8(m.1H), 3.5–4.0(m.4H), 2.2(s.3H). | 181.5–183.5 |
| 8 | COCH₃ | —NCH₂CH₂CH₂OH | 8.8(b.1H), 8.5(d.d.1H), 7.9(d.d.1H), 7.65(s.1H), 6.9–7.5(m.2H), 4.25(b.1H), 3.5–4.0(m.4H), 2.15(s.3H), 1.6–2.05(m.2H). | 118.5–119.5 |
| 9 | COCH₃ | —NHCH₂CHCH₂OH <br> \|<br>OH | 8.5(d.d.1H), 7.9(d.d.1H), 7.5(s.1H), 7.35(d.d.1H), 4.2–4.9(m.2H), 3.1–4.0(m.7H), 2.1(s.3H). | 174.5–175.0 |
| 10 | COCH₃ | —NHCH₂CH₂—C₆H₅ | 8.4(d.d.1H), 8.1(b.1H), 7.8(d.d.1H), 7.6(s.1H), 7.0–7.4(m.6H), 3.5–4.1(m.2H), 2.8–3.2(t.2H), 3.1(s.3H). | 163.0–166.0 |
| 11 | COCH₃ | —NHCH₂CH₂—C₆H₄—OCH₃ | 8.4(d.d.1H), 8.1(bs.1H), 7.8(d.d.1H), 7.6 (s.1H), 7.3(d.d.1H), 7.1(d.2H), 6.7(d.2H), 3.7(s.3H), 3.5–4.0(m.2H), 2.9(t.2H), 2.1(s.3H). | 143.0–144.0 |
| 12 | COCH₃ | —NHCH₂—(pyridyl) | 8.45–8.65(m.2H), 6.9–8.1(m.8H), 4.85(d.2H), 2.15(s.3H). | 176.0–179.0 (decomp.) |

TABLE 5-continued

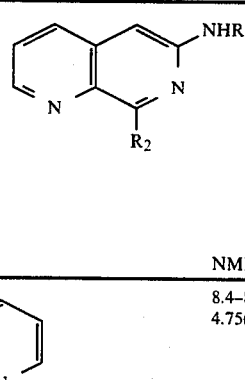

| Compound No. | R₁ | R₂ | NMR (δ ppm) | Melting point (°C.) HCl salt |
|---|---|---|---|---|
| 13 | COCH₃ | 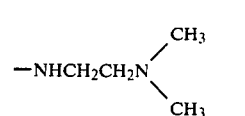 -NHCH₂- | 8.4–8.7(m.3H), 7.0–8.1(m.7H), 4.75(d.2H), 2.2(s.3H). | 177.0– 180.0 (decomp.) |
| 14 | COCH₃ | —NHNH₂ | 10.1(b.2H), 8.6(d.d.1H), 8.1(d.d.1H), 7.6(s.1H), 7.4(d.d.1H), 4.0–4.8(m.1H), 2.1(s.3H). | 231.0– 233.0 |
| 15 | COCH₃ | —NHCH₂CH₂N(CH₃)₂ | 8.5(d.d.1H), 7.8–8.0(m,2H), 7.6(s.1H), 7.0–7.5(m.2H), 3.6(q.2H), 2.6(t.2H), 2.3(s.6H), 2.2(s.3H). | 152.5– 153.0 |
| 16 | COCH₃ | —N(CH₃)₂ | 8.6(d.d.1H), 7.95(d.d.1H), 7.7(s.1H), 7.35(d.d.1H), 3.4(s.6H), 2.2(s.3H). | 152.5– 153.0 |
| 17 | COCH₃ | —N(CH₂CH₂OH)₂ | 8.3–8.6(m.2H), 8.0(d.d.1H), 7.8(s.1H), 7.35(d.d.1H), 5.7(b.2H), 3.9(s.8H), 2.2(s.3H). | 157.5– 158.5 |
| 18 | COCH₃ | 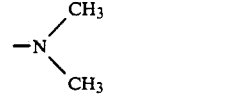 morpholino | 8.65(d.d.1H), 7.9–8.1(m.2H), 7.9(s.1H), 7.4(d.d.1H), 3.95(s.8H), 2.2(s.3H). | 214.5– 215.5 |
| 19 | COCH₃ | 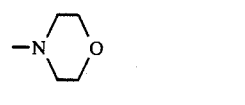 4-methylpiperazinyl | 8.6(d.d.1H), 8.0(d.d.1H), 7.9(s.1H), 7.4(d.d.1H), 3.9–4.2(m.4H), 2.5–2.9(m.4H), 2.3(s.3H), 2.2(s.3H). | 174.0– 177.0 |
| 20 | COCH₃ | 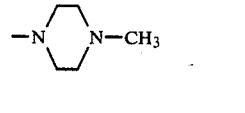 4-phenylpiperazinyl | 8.6(d.d.1H), 7.8–8.1(m.3H), 6.8–7.5(m.6H), 4.0–4.3(m.4H), 3.2–3.6(m.4H), 2.2(s.3H). | 214.0– 215.0 |
| 21 | —COCH₃ | 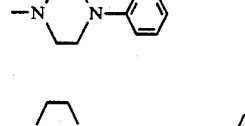 | 8.6(d.d.1H), 8.0(d.d.1H), 7.9(s.1H), 7.8(b.1H), 7.6(d.1H), 7.4(d.d.1H), 6.8(d.1H), 6.7(s.2H), 3.6–4.2(m.17H), 2.1(s.3H) | 208.5– 209.0 |
| 22 | —COCH₃ | 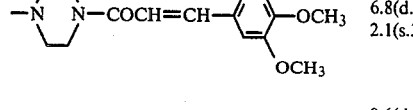 | 8.6(d.d.1H), 8.2(b.1H), 7.9(d.d.1H), 7.8(s.1H), 7.3(d.d.1H), 3.9–4.2(m.4H), 3.7(t.2H), 3.15(s.1H), 2.5–2.9(m,6H), 2.2(s.3H). | 153.5– 155.0 |
| 23 | —COCH₂CH₃ | 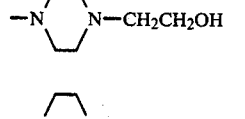 | 8.6(d.d.1H), 7.9(d.d.1H), 7.8(b.1H), 7.75(s.1H), 7.3(d.d.1H), 3.9–4.2(m.4H), 3.7(t.2H), 2.5–3.0(m.6H), 2.45(q.2H), 1.35(t.3H). | 147.5– 148.5 |
| 24 | —CO(CH₂)₄CH₃ | 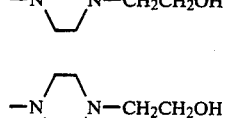 | 8.6(d.d.1H), 7.9(d.d.1H), 7.8(s.1H), 7.7(b.1H), 7.3(d.d.1H), 3.9–4.2(m.4H), 3.7(t.2H), 2.2–3.0(m.8H), 1.1–2.0(m.6H), 0.9(t.3H). | 100.0– 102.0 |
| 25 | —CO(CH₂)₆CH₃ | 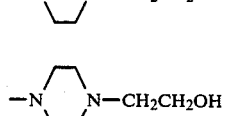 | 8.6(d.d.1H), 8.0(b.1H), 7.9(d.d.1H), 7.85(s.1H), 7.3(d.d.1H), 3.9–4.2(m.4H), 3.7(t.2H), 2.2–2.9(m.8H), 1.1–2.0(m.10H), 0.9(t.3H). | 174.0– 179.0 (decomp.) |

TABLE 5-continued

[Structure: naphthyridine with NHR₁ at one position and R₂ at another]

| Compound No. | R₁ | R₂ | NMR (δ ppm) | Melting point (°C.) HCl salt |
|---|---|---|---|---|
| 26 | −CO−C₆H₅ | −N(piperazinyl)−CH₂CH₂OH | 8.6(d.d.1H), 8.4(b.1H), 8.0(s.1H), 7.88(m.3H), 7.5(m.4H), 4.03(m.4H), 3.65(t.2H), 2.3–3.0(m.7H). | 210–215 |
| 27 | −CO−C₆H₄−CH₃ | −N(piperazinyl)−CH₂CH₂OH | 8.48(d.d.1H), 8.32(b.1H), 7.9(s.1H), 7.72(m.1H), 7.7(d.2H), 7.25(m.1H), 7.12(d.2H), 3.97(t.4H), 3.6(t.2H), 2.92(s.1H), 2.68(m.6H), 2.36(s.3H). | 252–260 (decomp.) |
| 28 | −CO−C₆H₄−OCH₃ | −N(piperazinyl)−CH₂CH₂OH | 8.50(d.d.1H), 8.35(b.1H), 7.93(s.1H), 7.82(m.1H), 7.80(d.2H), 7.27(m.1H), 6.85(d.2H), 3.98(t.4H), 3.75(s.3H), 3.62(t.2H), 2.90(s.1H), 2.68(m.6H). | 240–249 (decomp.) |
| 29 | −CO−C₆H₄−Cl | −N(piperazinyl)−CH₂CH₂OH | 8.47(d.d.1H), 8.46(b.1H), 7.88(s.1H), 7.8(m.1H), 7.74(d.2H), 7.27(m.1H), 7.26(d.2H), 3.98(t.4H), 3.62(t.2H), 2.98(s.1H), 2.65(m.6H). | 248–251 (decomp.) |
| 30 | −CO−C₆H₄−F | −N(piperazinyl)−CH₂CH₂OH | 8.55(d.d.1H), 8.45(b.1H), 7.95(s.1H), 7.7–8.2(m.3H), 6.85–7.5(m.3H), 4.0(m.4H), 3.65(t.2H), 2.3–3.1(m.7H). | 243–248 (decomp.) |
| 31 | −CO−C₆H₄−OH | −N(piperazinyl)−CH₂CH₂OH | 8.94(b.1H), 8.66(d.d.1H), 7.98(d.d.1H), 7.96(s.1H), 7.70(d.d.1H), 7.3–7.55(m.2H), 6.8–7.2(m.3H), 4.07(t.4H), 3.72(t.2H), 2.63(m.6H). | 149–152 (decomp.) |
| 32 | −COCH=CH−C₆H₅ | −N(piperazinyl)−CH₂CH₂OH | 8.65(d.d.1H), 8.12(b.1H), 8.02(s.1H) 8.0(d.d.1H), 7.8(d.1H), 7.10–7.62(m.6H), 6.60(d.1H), 4.02(m.4H), 3.68(t.2H), 2.7(m.7H). | 248–255 (decomp.) |
| 33 | H | −OC₄H₉ | 0.9–2.0(m.7H), 4.2(b.2H), 4.4(t.2H), 6.0(s.1H), 7.1(d.d.1H), 7.55(d.d.1H), 8.4(d.d.1H). | 128–129.5 |
| 34 | −COCH₃ | −OC₂H₅ | 1.5(t.3H), 2.2(s.3H), 4.5(q.2H), 7.3(d.d.1H), 7.85(s.1H), 7.9(d.d.1H), 8.1(d.d.1H) (CDCl₃ + DMSO-d₆). | 258–260 |
| 35 | −COCH₃ | NHCH₂CH₂−C₆H₃(OCH₃)₂ | 1.85(s.1H), 2.2(s.3H), 2.85(t.2H), 3.65(t.2H), 3.7(s.3H), 3.75(s.3H), 6.5–6.9(m.3H), 7.2(d.d.1H), 7.45(s.1H), 7.55(d.d.1H), 8.3(d.d.1H). | 133.5–134.5 |
| 36 | −COCH₃ | −OCH₃ | 2.2(s.3H), 4.05(s.3H), 7.3(d.d.1H), 7.5–7.7(m.1H), 7.85(s.1H), 7.9(d.d.1H), 8.1(d.d.1H). | 249–252 |
| 37 | −CO(CH₂)₆CH₃ | −N(CH₃)₂ | 1.85(t.3H), 1.0–2.0(m.10H), 2.35(t.2H), 3.35(s.6H), 7.2(d.d.1H), 7.65(s.1H), 7.8(d.d.1H), 8.5(d.d.1H). | 80–80.5 |
| 38 | −CO−C₆H₃(OCH₃)₂ | −N(CH₃)₂ | 3.4(s.6H), 3.85(s.3H), 3.90(s.3H), 6.75(d.1H), 7.1–7.35(m.2H), 7.4(s.1H), 7.8(d.d.1H), 7.85(s.1H), 8.2(b.1H), 8.5(d.d.1H). | 151.5–152.5 |

EXAMPLE 5

Tablet

| | |
|---|---|
| 1,7-Naphthyridine Derivative (Compound No. 16) | 5 mg |

| | |
|---|---|
| -continued | |
| D-Mannitol | 100 mg |
| Crystalline cellulose | 30 mg |
| Starch | 55 mg |
| Calcium carboxymethylcellulose | 8 mg |
| Talc | 5 mg |
| Magnesium stearate | 2 mg |
| TOTAL | 200 mg |

A tablet having the above ingredients in the above-specified amounts per tablet was prepared by a method known per se in the art.

EXAMPLE 6

Capsule

By a method known per se in the art, granules of the following composition and amount were prepared. They were then filled in a single piece of No. 4 capsule.

| | |
|---|---|
| 1,7-Naphthyridine Derivative (Compound No. 8) | 5 mg |
| Corn starch | 25 mg |
| Crystalline cellulose | 100 mg |
| TOTAL | 130 mg |

EXAMPLE 7

Injection

Fifty injections, each filled in a 2-ml amber-colored ampoule, were produced from the following ingredients in the following amounts by a method known per se in the art.

| | |
|---|---|
| 1,7-Naphthyridine Derivative (hydrochloride of Compound No. 8) | 250 mg |
| Physiological saline | balance to 100 ml in total |

EXAMPLE 8

Suppository

By a method known per se in the art, a single piece of suppository was produced by melting and mixing the following ingredients in the following amounts and then molding and solidifying the resultant mixture.

| | |
|---|---|
| 1,7-Naphthyridine Derivative (Compound No. 8) | 5 mg |
| Cacao butter | 1195 mg |
| TOTAL | 1200 mg |

Having now fully described the invention, it will be apparent to one of ordinary skill in the art that many changes and modifications can be made thereto without departing from the spirit or scope of the invention as set forth herein.

What is claimed as new and is secured by Letters Patent is:

1. A 1,7-naphthyridine derivative represented by the following general formula (I):

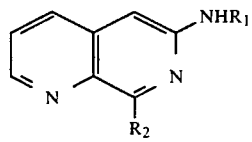

wherein
$R_1$ means a $COR_3$ group; in which $R_3$ is an alkyl group, a phenyl group which may optionally be substituted by one or more alkyl, alkoxy, hydroxyl and/or halogen, or a styryl group, and
$R_2$ denotes a piperidino or morpholino group, an

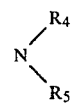

group, in which $R_4$ is a hydrogen atom or an alkyl or hydroxyethyl group and $R_5$ is an alkyl, amino, hydroxyethyl, hydroxypropyl, dihydroxypropyl, dialkylaminoethyl, phenylethyl, alkoxyphenylethyl or pyridylmethyl group, or an

group, in which $R_6$ is an alkyl, phenyl or hydroxyethyl group or a cinnamoyl group which may optionally be substituted by one or more alkyl, alkoxy and/or hydroxyl groups and/or halogen atoms; or an acid addition salt thereof.

2. A pharmaceutical composition containing, as an effective ingredient, a 1,7-naphthyridine derivative represented by the following general formula (I):

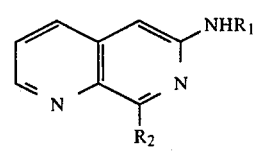

wherein
$R_1$ means a $COR_3$ group; in which $R_3$ is an alkyl group, a phenyl group which may optionally be substituted by one or more alkyl, alkoxy, hydroxyl and/or halogen, or a styryl group, and
$R_2$ denotes a piperidino or morpholino group, an

group, in which $R_4$ is a hydrogen atom or an alkyl or hydroxyethyl group and $R_5$ is an alkyl, amino, hydroxyethyl, hydroxypropyl, dihydroxypropyl, dialkylaminoethyl, phenylethyl, alkoxyphenylethyl or pyridylmethyl group, or an

group, in which $R_6$ is an alkyl, phenyl or hydroxyethyl group or a cinnamoyl group which may optionally be substituted by one or more alkyl, alkoxy and/or hydroxyl groups and/or halogen atoms; or an acid addition salt thereof in association with a pharmaceutically acceptable carrier.

* * * * *